(12) United States Patent
Fields, Jr. et al.

(10) Patent No.: US 6,187,937 B1
(45) Date of Patent: Feb. 13, 2001

(54) PREPARATION OF N-PHENYL-BENZOQUINONEIMINE FROM HYDROXYDIPHENYLAMINES

(75) Inventors: Donald L. Fields, Jr., Copley, OH (US); Michael K. Stern, Clayton, MO (US); Jayant Shivji Lodaya, Akron, OH (US)

(73) Assignee: Flexsys America L.P., Akron, OH (US)

( * ) Notice: Under 35 U.S.C. 154(b), the term of this patent shall be extended for 0 days.

(21) Appl. No.: 09/264,989

(22) Filed: Dec. 23, 1998

Related U.S. Application Data
(60) Provisional application No. 60/071,690, filed on Jan. 16, 1998.

(51) Int. Cl.$^7$ .................................................. C07C 50/04
(52) U.S. Cl. ......................... 552/302; 552/301; 552/302
(58) Field of Search ...................................... 552/301, 302

(56) References Cited

U.S. PATENT DOCUMENTS

| | | | |
|---|---|---|---|
| 4,158,643 | 6/1979 | Sinha | 252/447 |
| 4,264,776 | 4/1981 | Hershman et al. | 564/384 |
| 4,624,937 | 11/1986 | Chou | 502/180 |
| 4,968,843 | 11/1990 | Cottman | 564/397 |
| 5,053,540 | 10/1991 | Cottman | 564/397 |
| 5,068,439 | 11/1991 | Cottman | 564/434 |
| 5,189,218 | 2/1993 | Desmurs et al. | 564/272 |
| 5,371,289 | 12/1994 | Cottman et al. | 564/396 |

FOREIGN PATENT DOCUMENTS

| | | | |
|---|---|---|---|
| 448 899A1 | 10/1991 | (EP) | C07C/209/28 |
| 617 004A1 | 9/1994 | (EP) | C07C/209/18 |

OTHER PUBLICATIONS

Chem. Abstract 87:133491, Ram, Nathu et al., *Automation of p–hydroxydiphenylamine*, Tetrahedron, 33 (8), 887–90, 1977 (Abstract only).

Primary Examiner—Sabiha N Qazi
(74) Attorney, Agent, or Firm—Louis A. Morris

(57) ABSTRACT

A hydroxydiphenylamine compound can be converted to an N-phenylquinoneimine by reacting the hydroxydiphenylamine with oxygen or an oxygen containing gas in the presence of a modified activated carbon catalyst, the catalyst having had surface oxides removed therefrom.

21 Claims, No Drawings

PREPARATION OF N-PHENYL-BENZOQUINONEIMINE FROM HYDROXYDIPHENYLAMINES

This application claims the benefit of U.S. Provisional Application No. 60/071,690, filed Jan. 16, 1998.

FIELD OF THE INVENTION

This invention relates to a novel process for the preparation of N-phenyl-benzoquinoneimines from their corresponding hydroxydiphenylamines using an activated carbon catalyst which has had surface oxides removed therefrom.

BACKGROUND OF THE INVENTION

The class of cyclic enones is well known in organic chemistry. Best known examples of cyclic-enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, Kirk-Othmer Encyclopedia of Chemical Technology, Third ed., Vol. 19, pages 572–605, John Wiley & Sons, New York, 1982.

The synthesis of quinones is well documented. See, for example, J. Cason, *Synthesis of Benzoquinones by Oxidation,* in Organic Synthesis, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or sometimes from quinic acid. The reagents generally used for the oxidation are dichromate/sulfuric acid mixture, ferric chloride, silver (II) oxide or ceric ammonium nitrate. Such methods are generally performed in solvents which may need elaborate waste disposal procedures. Some processes may also take several hours for completion of the reaction.

Thus, some of the prior art processes utilize a catalytic agent to achieve an acceptable reaction rate while other processes proceed without catalysts. The process according to the present invention utilizes an oxidation mechanism which provides extremely high conversion, high selectivity, and fast reaction rates.

A prior art process which utilizes a catalyst in the preparation of an N-phenylquinone-imine compound is disclosed by Desmurs, et al. in U.S. Pat. No. 5,189,218. The process of Desmurs, et al., which converts a N-(4-hydroxyphenyl) aniline into N-phenylbenzoquinone-imine, utilizes a manganese, copper, cobalt, and/or nickel compound as a catalyst in an oxidation type reaction.

Other processes which convert hydroxydiphenylamines to N-phenylquinone-imines via stoichiometric oxidation using potassium or sodium dichromate catalysts are disclosed by Cottman in U.S. Pat. No. 4,968,843, U.S. Pat. No. 5,068,439, U.S. Pat. No. 5,053,540, U.S. Pat. No. 5,371,289, EP 448,899 and EP 617,004.

Denisov, et al. (*Bull. Acad. Sci. USSR Div. Chem. Sci.,* 37 (10), 1988) disclose preparation of N-phenylquinone-imine by reacting 4-anilino-phenol (4-hydroxydiphenylamine) with an $MnO_2$ catalyst in a benzene solvent system.

Ram et al. (*Tetrahedron,* 33(8), 887–90, 1977) teach a non-catalytic autoxidation reaction process for conversion of p-hydroxydiphenylamine to N-phenyl-p-benzoquinone-imine.

The above process of Desmurs, et al., which uses a metal catalytic component, along with any other processes which utilize a metal catalyst, have several drawbacks. Not only are the metal catalysts relatively expensive, they raise important environmental concerns. For example, effluent streams and products can be contaminated by such metals. Further, recovery of the catalyst for reuse can be prohibitively expensive.

Various non-heavy metal catalysts are known in the art. For example, activated carbon catalysts, which are typically prepared by heating carbon to high temperatures (800° C. to 900° C.) with steam or with carbon dioxide to bring about a porous particulate structure and increased surface area, are well known oxidation catalysts. U.S. Pat. No. 4,264,776, for example, discloses and claims a process for preparing secondary amines by catalytic oxidation of tertiary amines using an activated carbon catalyst.

U.S. Pat. No. 4,158,643 teaches a method for oxidation modification of an activated carbon support in which oxygen is added to the surface of the activated carbon, and then the carbon support is impregnated with an inert hydrophobic compound. The carbon support, which may be any commercially available activated carbon for vapor phase activation use, is useful in oxidizing carbon monoxide in the presence of sulfur dioxide for an extended period of time.

U.S. Pat. No. 4,624,937 provides a method for preparing activated carbon for catalytically oxidizing tertiary amines or secondary amines in the presence of oxygen or an oxygen-containing gas to selectively produce secondary or primary amines. The method of U.S. Pat. No. 4,624,937 comprises the step of treating the carbon catalyst to remove oxides from the surface thereof.

Thus, it can be seen that processes for preparing quinoneimines from hydroxydiphenylamines are known. Additionally, the use of various carbon catalysts, including activated carbon, in chemical reactions is known. However, in the conversion of hydroxydiphenylamine to an N-phenyl-benzoquinoneimine, the use of a modified activated carbon compound as an oxidation catalyst has not heretofore been suggested.

SUMMARY OF THE INVENTION

It has now been discovered that a hydroxydiphenylamine compound can be converted into its corresponding N-phenyl-benzoquinoneimine by reacting the hydroxydiphenylamine with oxygen or an oxygen containing gas in the presence of a modified activated carbon catalyst.

The modified activated carbon catalyst of the present invention has been treated to remove oxides from the surface thereof. Such a modified carbon catalyst allows the conversion of hydroxydiphenylamine to the corresponding N-phenyl-benzoquinoneimine in almost quantitative (HPLC) yields.

In contrast to prior art, an advantage of using the process of the present invention is that the conversion of hydroxydiphenylamine to the corresponding N-phenyl-benzoquinoneimine is nearly quantitative. Thus, very little waste material remains upon completion of the reaction.

Another advantage realized when using the modified activated carbon catalyst set forth above is that the modified activated carbon catalyst not only is recyclable, but it also avoids the drawbacks associated with metal catalysts which include high cost, product contamination and environmental waste concerns.

An additional advantage is that the modified activated carbon catalysts as set forth herein provide a faster, more complete reaction compared to commercially available activated carbon catalysts in the conversion of hydroxydiphenylamines to N-phenyl-benzoquinoneimines.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for conversion of hydroxydiphenylamines to N-phenyl-benzoquinoneimines.

In accordance with the object of the invention, in a first embodiment, an ortho- or para-hydroxydiphenylamine according to Formula I:

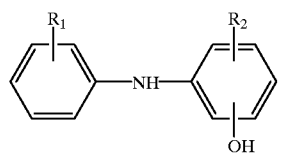

I wherein $R_1$ and $R_2$ are independently selected from hydrogen, hydroxyl, alkyl, aryl, aralkyl, alkaryl, cycloalkyl, heterocycle, acyl, aroyl, carbamyl, cyano, alkoxy, halogen, ether, thiol, amino, alkylamino, and arylamino; is reacted in the presence of oxygen or an oxygen containing gas and optionally, a solvent and heat, further in the presence of a modified activated carbon catalyst which has had the surface oxides removed therefrom.

The reaction produces a corresponding N-phenyl-benzoquinone-imine according to Formula IIA or IIB:

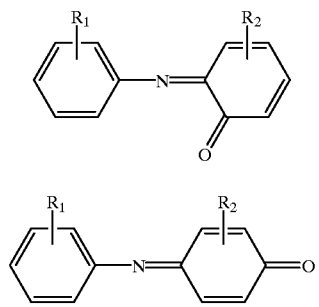

IIA

IIB

The reaction is represented as follows:

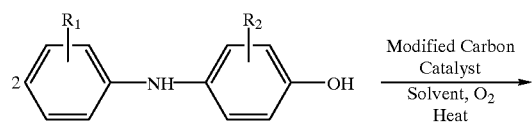

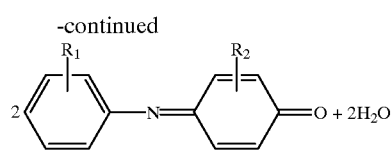

Examples of satisfactory radicals for $R_1$ and $R_2$ are linear or branched alkyls such as methyl, ethyl, propyl, butyl, pentyl, hexyl, heptyl, octyl, nonyl, decyl, dodecyl, and the like; aryls such as phenyl, naphthyl, anthracyl, tolyl, ethylphenyl, and the like; cycloalkyls such as cyclobutyl, cyclopentyl, cyclohexyl, cyclooctyl, and the like. Other examples include allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, 3-mercaptopropionyl, mercaptapyridazine, 2-mercaptobenzothiazole, caproyl, benzoyl, phthaloyl, terephthaloyl, aminocarbonyl, carbethoxy, carbonyl, formyl, and the like. These are merely exemplary radicals and are in no way intended to limit the scope of the invention.

The modified activated carbon catalyst, described above, is prepared by removing both acidic and basic surface oxides from the surfaces of a carbon catalyst. A method for making the modified activated carbon catalyst is set forth in U.S. Pat. No. 4,624,937.

According to U.S. Pat. No. 4,624,937, a carbon material, such as those described in U.S. Pat. No. 4,264,776, is initially provided.

Ordinarily, the initial carbon catalyst used in preparing the modified carbon catalyst is a commercially available activated carbon with a carbon content ranging from about 10% for bone charcoal to about 98% for some wood chars and nearly 100% for activated carbons derived from organic polymers. The noncarbonaceous matter in commercially available carbon materials will normally vary depending on such factors as precursor origin, processing, and activation method. The treatment process can be accomplished by a single or a multistep scheme which in either case results in an overall chemical reduction of oxides on the carbon surface, i.e., a reduction or removal of acidic oxides from the carbon surface.

As used herein, the term "oxides" is intended to mean carbon functional groups which contain oxygen atoms as well as hetero-atom functional groups which contain oxygen atoms. Other hetero-atom functional groups which do not contain oxygen atoms may also be removed from the surface of the carbon material during treatment.

In a two-step scheme, the carbon material can be first treated with an oxidizing agent such as, for example, liquid nitric acid, nitrogen dioxide, $CrO_3$, air, oxygen, $H_2O_2$, hypochlorite, or a mixture of gases obtained by vaporizing nitric acid. The treatment can be accomplished using either a gas or a liquid oxidizing agent. Where a liquid is used, concentrated nitric acid containing from about 10 to about 80 g. $HNO_3$ per 100 g. of aqueous solution is preferred. Preferred gaseous oxidants include oxygen, nitrogen dioxide, and nitric acid vapors. A particularly effective oxidant is nitric acid in the vapor phase which includes nitric acid carried into the vapor phase by an entraining gas as well as the vapors obtained by distilling liquid nitric acid. With a liquid oxidant, temperatures from about 60° C. to about 90° C. are appropriate, but with gaseous oxidants, it is often advantageous to use temperatures of about 50° C. to about 500° C. or even higher for the treatment step.

The treatment can be achieved by placing carbon from a manufacturer in a round bottom flask which contains a magnetic stirring bar. Liquid nitric acid is selected as the oxidizing agent for illustration. The amount of carbon used is determined by the percent carbon load desired (% carbon load %. of carbon used per 100 ml of nitric acid solution) and the nitric acid solution volume to be used. Ordinarily, 1 to 200 g. of carbon per 100 ml of nitric acid or other liquid oxidizing agent is satisfactory. Temperature control can be provided by any suitable means. A condenser and scrubber can be connected to the round bottom flask as desired. A calculated volume of water, preferably deionized water, is added to the carbon, followed by sufficient (69–71%) nitric acid to achieve the desired nitric acid solution. The carbon and nitric acid solution are then stirred for the desired period at the desired temperature.

After stirring, the carbon is filtered, and the resulting wet cake may or may not be washed and/or dried prior to pyrolysis.

The time during which the carbon is treated with the oxidant can vary widely from about 5 minutes to about 10 hours. Preferably, a reaction time of about 30 minutes to about 6 hours is satisfactory. When concentrated nitric acid is the oxidant, a contact time of about 30 minutes to about 3 hours is satisfactory.

In a second step, the oxidized carbon material is pyrolyzed, i.e., heat treated, at a temperature in the range of about 500° C. to about 1500° C., preferably from about 800° C. to 1200° C.

It is preferred to conduct the pyrolysis in an inert gas atmosphere, such as nitrogen, argon, or helium.

Wet cake or dry carbon is placed in a ceramic pyrolysis dish which together are placed in a quartz tube. Nitrogen is passed through water at about 70° C., then through the quartz tube during pyrolysis. A dry, static nitrogen atmosphere is maintained after flushing the quartz tube with several tube volumes of dry nitrogen prior to pyrolysis. The quartz tube containing the pyrolysis dish is placed in a suitable pyrolyzer apparatus at about 930° C. for the desired period, followed by cooling while maintaining the nitrogen atmosphere.

Pyrolysis can last anywhere from about 5 minutes to 60 hours, although 10 minutes to 6 hours is normally satisfactory. The shorter times are preferred for economic reasons because, as might be expected, continued exposure of the carbon to elevated temperatures for prolonged periods can result in a poor carbon catalyst for the oxidation. Pyrolysis may be initiated in a slightly moist atmosphere or an atmosphere which contains $NH_3$ as this appears to produce a more active catalyst in a shorter time.

Alternatively, the treatment is accomplished in a single step by pyrolyzing the carbon material as described above while simultaneously passing a gas stream comprised of $NH_3$ and an oxygen-containing gas, e.g., $H_2O/NH_3$, through the carbon. The flow rate of the gas stream should be fast enough to achieve adequate contact between fresh gas reactants and the carbon surface, yet slow enough to prevent excess carbon weight loss and material waste. Many $NH_3$/oxygen-containing gas mixtures can be used such as, for example, $NH_3/CO_2$, $NH_3/O_2$, $NH_3/H_2O$ and $NH_3/NOx$, provided the gas mixture achieves the desired result. Ordinarily, the oxygen-containing gas/$NH_3$ ratio can range from 0:100 to 90:10. Furthermore, nitrogen can be used as a diluent to prevent severe weight loss of the carbon in high oxygen-containing gas concentrations. Ammonia is a basic gas, and, as such, is believed to assist the decomposition of the various oxide groups on the surface of the carbon material. Any other chemical entity which will generate $NH_3$ during pyrolysis should also prove satisfactory as an $NH_3$ source. For economic reasons, an $NH_3/H_2O$ gas stream is most preferred.

The carbon materials treated according to the procedure set forth above, when used in the catalytic oxidation of a hydroxydiphenylamine to the corresponding N-phenylbenzoquinoneimine, demonstrates a fast, efficient conversion reaction without the drawbacks associated with using the heavy metal catalysts of the prior art processes.

The catalyst loading concentration of the present invention is generally about 0.5% to about 25.0% (wt/wt hydroxydiphenylamine). Preferably, about 10% (wt/wt hydroxydiphenylamine) catalyst is used in the reactions according to the present invention.

Various solvents may be used in any of the reactions in accordance with the present invention. Examples of solvents which may be used in the reactions according to the present invention include, but are not limited to, alcohols such as methanol, ethanol, isopropanol, methyl isobutyl carbinol, ethylene glycol, etc.; ketones such as acetone and methyl isobutyl ketone, cyclohexanone, 5-methyl-2-hexanone, 5-methyl-3-heptanone; aliphatic and/or aromatic hydrocarbons such as alkanes, alkenes, toluene and xylene; nitriles such as acetonitrile; halogenated solvents such as chloroform, methylene chloride, and carbontetrachloride; and other solvents such as N-methylpyrrolidone, THF, ethylacetate, dimethylformamide, and dimethylsulfoxide, or any mixture of solvents would also be usable.

The starting material, a hydroxydiphenylamine (HDA), may be present at concentrations from about 1.0% to about 75.0%.

The reaction may take place at varying temperatures in a range of from about 0° C. to about 100° C. Preferably, the reaction temperature is in a range of from about 20° C. to about 80° C.

The reaction of the present invention takes place in an oxygen system. Oxygen pressure can be varied with an effective range being between atmospheric psig and 1500 psig. Preferably, the system is between 15 and 100 psig $O_2$. The oxygen concentration can range from about 100% $O_2$ to about 2% $O_2$ (using nitrogen or air dilution).

It is also possible to utilize a tertiary amine to accelerate the rate of reaction in the process of the present invention. Tertiary amines usable in the present invention include, but are not limited to, trialkyl- and triaryl-amines. The addition of a tertiary amine will result in a basic pH for the reaction. Preferably the pH is about pH8 to about pH9.

The present invention can be more clearly illustrated by the following example(s). The modified activated carbon catalyst used in the examples was prepared in accordance with the procedure set forth above.

EXAMPLE 1

A mixture of 5.0 g of 4-hydroxydiphenylamine (4-HDA), 0.5 g modified carbon catalyst and 200 mL methanol was charged to an autoclave. The reaction mixture was stirred and the autoclave, purged with oxygen, was then charged to 30 psig of oxygen at 20–25° C. The reaction mixture was then heated to 50° C. and maintained at 50° C. until the reaction was complete. As the reaction progressed, the oxygen pressure dropped. When oxygen pressure dropped to about 20 psig, more oxygen was charged to bring the pressure back to 30 psig. The reaction time was counted from the moment oxygen was charged to the autoclave. The reaction progress was monitored by analyzing samples using HPLC. When very little or no oxygen uptake was detectable and the HPLC analysis indicated disappearance of starting material 4-hydroxydiphenylamine, the product was filtered to separate the catalyst. The reaction took about 1 hour and the HPLC analysis of the mixture indicated 99.7 area % of the product N-phenyl-p-benzoquinoneimine (NPQI). The product can be isolated in greater than 90% yield. The product is brown solids with a melting point of 100–103° C.

Various isolation techniques well known in the art may be used to isolate the product according to the present invention including, but not limited to, crystallization, concentration and/or precipitation.

The catalyst and solvent recovered from the reaction can be recycled and reused in subsequent reactions.

EXAMPLE 2

This example teaches the effect of using triethylamine to increase the rate of reaction.

In accordance with procedure set forth in Example 1, a mixture of 5.0 g of 4-hydroxydiphenylamine (4-HDA), 0.5 g modified carbon catalyst, 1.5 g triethylamine and 200 ml methanol was charged to an autoclave. The same procedure as described in Example 1 was employed. The reaction took 20 minutes and the HPLC analysis of the mixture indicated 98.6 area % of the product N-phenyl-p-benzoquinoneimine (NPQI).

Again, various isolation techniques well known in the art may be used to isolate the product according to the present invention including, but not limited to, crystallization, concentration and/or precipitation.

The catalyst and solvent recovered from the reaction can be recycled and reused in subsequent reactions.

EXAMPLE 3

In accordance with procedure set forth in Example 1, 5.0 g of 4-hydroxydiphenylamine (4-HDA) in 200 mL toluene and 0.5 g modified carbon catalyst were charged to an autoclave. The same procedure as described in Example 1 was employed. The reaction was carried out to completion in less than 1.25 hrs and the catalyst was separated from the product by simple filtration. HPLC analysis of the mixture indicated greater than 95 area % of the product N-phenyl-p-benzoquinoneimine.

A comparison of the following two examples clearly indicate the advantages of triethylamine on the rate of reaction.

EXAMPLE 4

A mixture of 5.0 g of 4-hydroxydiphenylamine (4-HDA), 0.5 g modified carbon catalyst and 200 mL methanol was charged to an autoclave. The reaction mixture was stirred and the autoclave, purged with oxygen, was then charged to 30 psig of oxygen at 21° C. The reaction mixture is was then maintained at 21° C. until the reaction was complete. As the reaction progressed, the oxygen pressure dropped. When oxygen pressure dropped to 20 psig, more oxygen was charged to bring the pressure back to 30 psig. The reaction time was counted from the moment oxygen was charged to the autoclave. The reaction progress was monitored by analyzing samples using HPLC. The following table summarizes the results

TABLE 1

| Sample No. | Time (minutes) | Area % 4-HDA | Area % NPQI |
| --- | --- | --- | --- |
| 1 | 10 | 31.1 | 68.2 |
| 2 | 20 | 30.1 | 69.3 |
| 3 | 30 | 14.9 | 83.1 |

TABLE 1-continued

| Sample No. | Time (minutes) | Area % 4-HDA | Area % NPQI |
| --- | --- | --- | --- |
| 4 | 40 | 13.8 | 85.6 |
| 5 | 50 | 8.15 | 90.4 |
| 6 | 60 | 7.5 | 90.9 |
| 7 | 70 | 5.4 | 94.2 |
| 8 | 80 | 3.6 | 96.1 |
| 9 | 90 | 3.3 | 94.6 |
| 10 | 100 | 1.6 | 97.5 |
| 11 | 110 | 0.85 | 98.6 |

When very little or no oxygen uptake was detectable and the HPLC analysis indicated disappearance of starting material 4-hydroxydiphenylamine, the product was filtered to separate the catalyst. The HPLC analysis of the mixture indicated 98.6 area % of the product N-phenyl-p-benzoquinoneimine (NPQI).

Again, various isolation techniques well known in the art may be used to isolate the product according to the present invention including, but not limited to, crystallization, concentration and/or precipitation.

The catalyst and solvent recovered from the reaction can be recycled and reused in subsequent reactions.

EXAMPLE 5

In accordance with procedure set forth in Example 4, a mixture of 5.0 g of 4-hydroxydiphenylamine (4-HDA), 0.5 g modified carbon catalyst, 200 mL methanol and 1.5 g triethylamine was charged to an autoclave. The reaction mixture was stirred and the autoclave, purged with oxygen, was then charged to 30 psig of oxygen at 21° C. The reaction mixture was then maintained at 21° C. until the reaction was complete. As the reaction progressed, the oxygen pressure dropped. When oxygen pressure dropped to 20 psig, more oxygen was charged to bring the pressure back to 30 psig. The reaction time was counted from the moment oxygen was charged to the autoclave. The reaction progress was monitored by analyzing samples using HPLC. The following table summarizes the results:

TABLE 2

| Sample No. | Time (minutes) | Area % 4-HDA | Area % NPQI |
| --- | --- | --- | --- |
| 1 | 10 | 18.3 | 80.5 |
| 2 | 20 | 8.7 | 90.5 |
| 3 | 30 | 3.7 | 93.9 |
| 4 | 40 | 2.1 | 96.9 |
| 5 | 50 | 1.3 | 98.3 |
| 6 | 60 | 0.77 | 99.2 |

When very little or no oxygen uptake was detectable and the HPLC analysis indicated disappearance of starting material 4-hydroxydiphenylamine, the product was filtered to separate the catalyst. The HPLC analysis of the mixture indicated 99.2 area % of the product N-phenyl-p-benzoquinoneimine (NPQI).

This clearly indicates that the rate of reaction in the presence of triethylamine is extremely faster in comparison to the one without it.

The N-phenyl-benzoquinoneimines of the present invention may be used as starting materials in the production of aminodiphenylamines. Para-aminodiphenylamines are used in the production of numerous rubber chemicals including antidegradants, gel inhibitors and polymerization inhibitors. Further, the N-phenyl-benzoquinoneimines also exhibit performance enhancement properties when used as rubber additives.

The invention has been described with reference to the preferred embodiments. Obviously, modifications and alterations will occur to others upon reading and understanding the preceding detailed description. It is intended that the invention be construed as including all such modifications and alterations in so far as they come within the scope of the appended claims or the equivalents thereof.

What is claimed is:

1. A process for preparing an N-phenylquinone-imine (NPQI) comprising oxidizing a corresponding hydroxydiphenylamine (HDA) in the presence of oxygen or an oxygen containing gas and a modified activated carbon catalyst, with said catalyst having been modified by having surface oxides removed therefrom.

2. The process of claim 1 wherein the hydroxydiphenylamine (HDA) is 4-hydroxydiphenylamine.

3. The process of claim 1 wherein the HDA is initially dissolved and/or mixed in a solvent.

4. The process of claim 3 wherein the solvent is an alcohol, ketone, aromatic/aliphatic hydrocarbon, nitrile, halogenated solvents, N-methylpyrrolidone, THF, ethylacetate, dimethylformamide, dimethylsulfoxide, water, or mixtures thereof.

5. The process of claim 4 wherein the alcohol solvent is selected from methanol, ethanol, isopropanol, methyl isobutyl carbinol and ethylene glycol.

6. The process of claim 1 wherein the reaction takes place at a temperature of from about 0° C. to about 100° C.

7. The process of claim 1 wherein a tertiary amine is further added to the reaction.

8. The process of claim 7 wherein the tertiary amine is triethylamine.

9. The process of claim 1 wherein the oxides are removed from the modified activated carbon catalyst surface by subjecting activated carbon to an oxidizing agent and then pyrolizing the activated carbon in an oxygen free atmosphere at a temperature in the range of about 500° C. to about 1500° C.

10. The process of claim 1 wherein the oxides are removed from the activated carbon catalyst surface by simultaneously pyrolizing the activated carbon in the presence of $NH_3$ and an oxygen containing gas that reacts with the oxides on the surface of the activated carbon at pyrolizing temperatures of about 500° C. to about 1500° C.

11. A process for production of an N-phenylquinone-imine comprising:

(a) providing a hydroxydiphenylamine in a solvent system;

(b) oxidizing said hydroxydiphenylamine in the presence of oxygen or an oxygen containing gas and a modified activated carbon catalyst to form an N-phenylquinone-imine;

(c) filtering the modified activated carbon catalyst from the resulting product of step (b); and (d) isolating the N-phenylquinone-imine from the resulting product of step (c);

wherein said modified activated carbon catalyst is characterized by having had surface oxides removed therefrom.

12. The process of claim 11 wherein the solvent is an alcohol, ketone, aromatic/aliphatic hydrocarbon, nitrile, halogenated solvents, N-methylpyrrolidone, THF, ethylacetate, dimethylformamide, dimethylsulfoxide, water, or mixtures thereof.

13. The process of claim 12 wherein the solvent is selected from methanol, ethanol, isopropanol, methyl isobutyl carbinol, ethylene glycol, toluene, xylenes, acetone, and methyl isobutyl ketone, or mixtures thereof.

14. The process of claim 11 wherein the reaction takes place at a temperature of from above 0° C. to about 150° C.

15. The process of claim 11 wherein the reaction takes place at a temperature of from about 15° to about 75° C.

16. The process of claim 11 wherein the pressure of the oxygen in the reaction is from atmospheric to about 1000 psig $O_2$.

17. The process of claim 11 wherein the pressure of the oxygen in the reaction is from about 20 psig to about 500 psig $O_2$.

18. The process of claim 11 wherein a tertiary amine is further added to the reaction.

19. The process of claim 18 wherein the tertiary amine is triethylamine.

20. The process of claim 11 wherein the oxides are removed from the modified activated carbon catalyst surface by subjecting activated carbon to an oxidating agent and then pyrolizing the activated carbon in an oxygen free atmosphere at a temperature in the range of about 500° to about 1500° C.

21. The process of claim 11 wherein the oxides are removed from the activated carbon catalyst surface by simultaneously pyrolizing the activated carbon in the presence of $NH_3$ and an oxygen containing gas that reacts with the oxides on the surface of the activated carbon at pyrolizing temperatures of about 500° C. to about 1500° C.

* * * * *